United States Patent

Alpegiani et al.

[11] Patent Number: 4,771,134
[45] Date of Patent: Sep. 13, 1988

[54] RING-OPENING PROCESS FOR PREPARING AZETIDINONE INTERMEDIATES

[75] Inventors: Marco Alpegiani; Angelo Bedeschi; Ettore Perrone, all of Milan, Italy

[73] Assignee: Farmitalia Carlo Erba S.p.A., Milan, Italy

[21] Appl. No.: 818,235

[22] Filed: Jan. 13, 1986

[30] Foreign Application Priority Data

Jan. 14, 1985 [BB] Barbados ............................. 8500831

[51] Int. Cl.$^4$ .................... C07D 205/08; C07B 45/06; C07F 7/18
[52] U.S. Cl. ..................................... 540/201; 540/357
[58] Field of Search ............................... 540/201, 357

[56] References Cited

FOREIGN PATENT DOCUMENTS 2343497 3/1975 Fed. Rep. of Germany .

Primary Examiner—Mark L. Berch
Attorney, Agent, or Firm—Wegner & Bretschneider

[57] ABSTRACT

Compounds of formula I

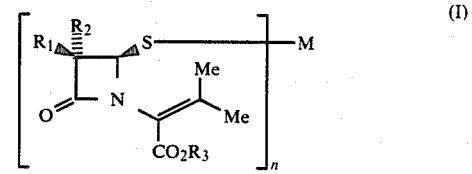

wherein $R_1$ and $R_2$ is each H, halo or an organic group, $R_3$ is H or organic group, n=1 or 2, M is a heavy mono- or divalent metal, or $M_2A$ wherein $M_2$ is a heavy divalent metal and A is an organic or inorganic group, are prepared by treating a starting penicillin in a solvent with a salt of $M_1$ or $M_2A$ in the presence of a base at a temperature of from −70° to 100° C.

9 Claims, No Drawings

RING-OPENING PROCESS FOR PREPARING AZETIDINONE INTERMEDIATES

The present invention provides a process for preparing azetidinones which are useful intermediates in the synthesis of β-lactam antibiotics, esp. penems. In particular, the present invention relates to a straightforward process for converting penem compounds of formula (II) into heavy metal azetidinone mercaptides of formula (I)

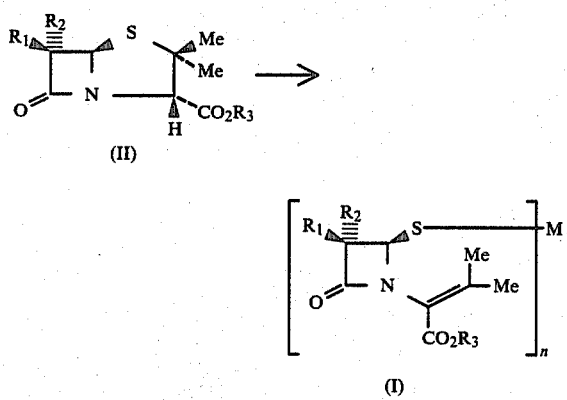

wherein:

$R_1$, $R_2$ are each independently hydrogen, halogen or an organic radical;

$R_3$ is hydrogen or an organic radical;

n is 1 or 2;

M is a heavy metal $M_1$ in the +1 or +2 oxidation state, or a group $M_2A$ wherein $M_2$ is a heavy metal in the +2 oxidation state and A is an organic or inorganic group.

When $R_1$, $R_2$ are halogen, they are preferably bromo.

When $R_1$, $R_2$ are organic radicals, they are preferably substituted or unsubstituted $C_1$–$C_4$ alkyl groups. The substituents may be chosen from hydroxy, amino, cyano, mercapto and trifluoromethyl groups, wherein the hydroxy, amino and mercapto group may be free or protected.

Examples of hydroxy, mercapto or amino protecting groups are, in particular, tri-($C_1$–$C_4$-alkyl)silyl ether, for instance, trimethylsilyl or dimethyl-tert-butyl-silyl groups; diaryl-$C_1$–$C_4$-alkyl silyl ethers, for example a diphenyl-tert-butyl-silyl group; halo-substituted alkyl carbonates such as 2,2,2 trichloroethoxycarbonyl and optionally substituted aryl-$C_1$–$C_4$ alkyl carbonates, for example benzyloxycarbonyl and p-nitrobenzyloxycarbonyl groups.

As used in the specification, the term "aryl" includes phenyl, phenyl substituted by one to three $C_{1-4}$-alkyl groups as tolyl, xylyl, cumyl or ethylphenyl or a nitro derivative thereof.

$R_1$, $R_2$ together can also be a group of the formula NR′R″, wherein R′ and R″ together form a $C_4$–$C_{15}$-dicarboxylic acyl group, which may be that of an alkanedicarboxylic acid or an aryldicarboxylic acid such as a phthalidyl group. R′ and R″ together can also form an organic $C_1$–$C_{15}$-ylidene residue including such arylidines as benzylidene, p-nitrobenzylidene or o-nitrobenzylidene.

In NR′R″, R′ can be hydrogen or tri-(lower alkyl)silyl, such as trimethylsilyl, and R″ can be an N-protecting group such as, preferably, trityl, formyl, lower-alkoxycarbonyl (such as t-butoxycarbonyl) or arylalkoxycarbonyl (such as p-nitrobenzyloxycarbonyl) or a group, R‴CO, wherein R‴ is $C_1$–$C_8$ alkyl or alkenyl optionally interrupted by O, S, CO or NH or substituted by an O, S or N function or by a halogen, cyano, heterocyclyl, hydroxy, carboxy, aryl or cycloalkyl group or R‴ is phenyl or heterocyclyl group.

The term heterocyclyl group, as used in this specification designates preferably a saturated or unsaturated pentatomic or hexatomic heterocyclic ring containing at least one heteroatom chosen from O, S and N. Said ring can be unsubstituted or substituted by one or more substituents selected from hydroxy, $C_1$–$C_4$ alkoxy, halogen, $C_1$–$C_4$ alkyl, mercapto, $C_1$–$C_4$ alkylthio and amino groups. A heterocyclic ring may be, for example, an optionally substituted thiazolyl, triazolyl, thiadiazolyl, tetrazolyl or triazinyl ring. Particularly preferred is a 3-aminothiazol-5-yl group.

The cycloalkyl group herein can be cyclopentyl or cycloheptyl, but preferably cyclohexyl. When $R_3$ is an organic radical, it may be any group which, together with the COO moiety, forms an esterified carboxyl group. Examples of carboxyl protecting groups $R_3$ are, in particular, $C_1$–$C_4$ alkyl groups, for instance methyl, ethyl or tert-butyl; halo-substituted $C_1$–$C_4$ alkyl groups, for example 2,2,2-trichloroethyl; $C_2$–$C_4$ alkenyl groups, for example allyl; optionally substituted aryl groups, for example phenyl and p-nitro-phenyl; optionally substituted aryl-$C_1$–$C_6$ alkyl groups, for example, benzyl, p-nitrobenzyl and p-methoxybenzyl, aryloxy $C_1$–$C_4$-alkyl groups, for example, phenoxymethyl; or groups such as benzhydryl, o-nitro-benzhydryl, acetonyl, trimethylsilyl, diphenyl-tert-butyl-silyl, and dimethyl-tert-butyl-silyl.

The definition of $R_3$ as an organic radical includes also any residue, including for instance such alkanoylmethyl groups as acetoxymethyl, pivaloyloxymethyl or arylcarboxy groups such as phtalidyl, leading to an ester group which is known to be hydrolized "in vivo" and to have favorable pharmacokinetic properties.

When M is a heavy metal $M_1$ in the +1 oxidation level, it is preferably $Ag^I$, and in the compounds of formula (I) n represents 1. When M is a heavy metal $M_1$ in the +2 oxidation level, it is preferably $Hg^{II}$, $Cu^{II}$, or $Pb^{II}$, and n represents 2. When M is a group $M_2A$, $M_2$ preferably represents the above heavy metals $M_1$ in the +2 oxidation level, A is preferably lower alkanoyloxy, such as acetoxy and mathoxycarbonyl, and more preferably an aryl such as phenyl, and n represents 1. A as an inorganic radical can be the ion of an inorganic acid such as the nitrate ion.

A particularly preferred substituted alkyl group that $R_1$ or $R_2$ may represent is 1-hydroxyethyl, wherein the hydroxyl is preferably protected as a silyl ether, e.g. 1-tert-butyldimethylsilyloxyethyl, or as a carbonate, e.g. 1-trichloroethoxycarbonyloxyethyl. Still preferably, $R_2$ represents such 1-hydroxyethyl groups and $R_1$ is hydrogen, or $R_1$ is hydroxyethyl and $R_2$ is bromo. Particularly preferred $R_3$ groups are methyl, trichloroethyl, p-nitrobenzyl, and acetoxymethyl. A particularly preferred heavy metal $M_1$ in the +1 oxidation level is $Ag^I$; a particularly preferred heavy metal $M_1$ in the +2 level is $Hg^{II}$.

A number of heavy metal salts of 4-mercaptoazetidinones are already known in the literature: R. Lattrell, *Liebigs Ann. Chem.*, 1974, 1937; A. Longo, P. Lombardi, C. Gandolfi and G. Franceschi, *Tetrahedron Lett.*, 22, 355 (1981); A. Martel, P. Dextraze, J. P. Daris, R. Saintonge, P. Lapointe, T. T. Conway, I. Monkovic, G. Kavadias, Y. Ueda, P. Elie, S. Patil, G. Caron, J. L. Douglas, M. Menard, and B. Belleau, *Can. J. Chem.*, 60, 942 (1982); F. Di Ninno, D. A. Muthard, R. W. Ratcliffe, and B. G. Christensen, *Tetrahydron Lett.*, 23, 3535 (1982); W. J. Leanza, F. Di Ninno, D. A. Muthard, R. R. Wilkering, K. J. Wildonger, R. W. Ratcliffe, and B. G. Christensen, *Tetrahedron Lett.*, 39, 2505 (1983); V. M. Girijavallabhan, A. K. Ganguly, P. Pinto, and R. Versace, *Tetrahedron Lett.*, 24, 3179 (1983); V. M. Girijavallabhan, A. K. Ganguly, P. Pinto, and R. Versace, *J. Chem. Soc., Chem. Commun.*, 908 (1983).

The usefulness of the compounds of formula (II) as intermediates in the field of β-lactam antibiotics is self-evident and in part documented in the literature referred to above. In fact, these salts can be readily alkylated, acylated and converted into a number of 4-azetidinylthioderivatives, according to a reaction known per se in the art. These derivatives, in turn, can be further manipulated on the azetidinone N-appendage to give monocyclic β-lactam antibiotics, e.g. monobactams:

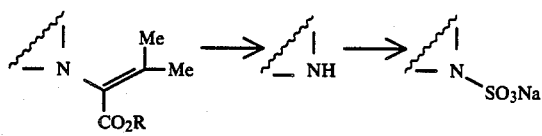

or bicyclic β-lactam antibiotics, e.g. penems and cephems.

A straightforward synthesis of compounds of formula (I) was still in demand, and it is now provided by the present invention. In fact, the methods known in the art and referred to above usually exploit an azetidinyl trityl sulphide or an azetidinyl tetrahydropyranil sulphide, which has to be synthesized through a multistep sequence either by total synthesis or from natural penicillins. Instead, the present invetion allows a direct conversion of penicillins into the compounds of formula (I) under mild, non-critical conditions. Moreover, the products (I) need not be isolated but can be further converted in situ to closer precursors of the target compounds.

According to the present invention, a solution of the starting penicillin of formula (II) in an aprotic organic solvent is treated with a strong, poorly nucleophilic base and an organic or inorganic salt of the heavy metal $M_1$ or of the $M_2A$ aggregate, wherein $M_1$, $M_2$ and A are as defined above. Preferred bases are diazabicyclononene (DBN), 1,4-diazabicyclooctane (DABCO) and diazabicycloundecene (DBU); preferred solvents are acetonitrile, dimethylformamide, benzene, dichloromethane; preferred heavy metal salts; are silver nitrate, silver perchlorate, silver acetate, mercury (II) acetate, methoxycarbonylmercury (II) acetate and phenyl mercury (II) chloride. Best yields are generally obtained in the temperature range of about −70° C./+100° C.; in several instances, the reaction is conveniently carried out at room temperature of 15°-20° C. As the poorly nucleophilic base there can be used teriary amines, preferably those sterically hindred. Protection from the light, an inert atmosphere and dry solvents are usually beneficial. If isolation of the product is desired, this can usually be performed by aqueous work-up; the compounds of formula (I) are usually extracted with standard organic solvents (e.g. ethyl acetate, dichloromethane). Alternatively, the heavy metal thiolates can be conveniently acylated or alkylated in situ, more preferably acylated.

Alkylation of the heavy metal mercaptides of formula I can be performed with reactive halides, such as methyl iodide, allyl bromide, benzyl bromide, and the like. Alkylation with α-halo acyl derivatives of formula III

wherein Hal is bromo or chloro, $R_4$ is hydrogen or lower alkyl, esp. methyl, X is oxygen, sulphur or a bond, and $R_5$ is an organic group, gives azetidinyl derivatives of formula IV

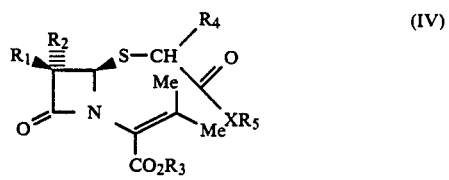

wherein $R_1$ $R_5$ and X are as defined above, which are useful for the synthesis of classical and non-classical cephalosporin derivatives (see, for example, J. H. C. Nayler et al., *J. Chem. Soc., Chem. Commun.*, 1973, 57 and 59).

A further object of the present invention is the acylation of heavy mercaptides of formula (I), which can be accomplished within a few minutes by the mere addition of an acylating agent of formula $R_6COY$, wherein Y represents a chlorine atom, an $OCOR_6$, $OCOR_6'$ or imidazolyl group.

The organic residue $R_6$ may be any of the substituents at 2-position of the penem framework; the penem are the final useful antibiotic compounds which are well known in the art, see Formula VII below. For example, $R_6$ can be an optionally substituted $C_1$-$C_4$ alkyl, methylphenyl, or methyl-$C_{5-7}$cycloalkyl group. The substituents are chosen from optionally protected hydroxy, amino or carbamoyloxy groups, halogen atoms, heterocyclylthio groups such as thiazolylthio, triazolylthio, thiadiazolylthio, tetrazolylthio, triazinylthio, tetrazolopyridazinylthio optionally substituted by a substituent chosen from amino, hydroxy, oxo and $C_1$-$C_4$ alkyl group optionally substituted and quaternary ammonio groups such as

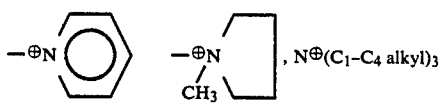

optionally substituted as above.

As the substituents of $R_6$, the hydroxy, amino or carbamoyloxy protecting groups, which may be present, are those usually employed in penicillins and cephalosporins for this kind of function.

They may be, for instance, optionally substituted, especially halo-substituted, acyl groups, e.g. acetyl, monochloroacetyl, dichloroacetyl, trifluoroacetyl, benzoyl or p-bromophenacyl; triarylmethyl groups, in particular triphenylmethyl; silyl groups, in particular trimethylsilyl, dimethyl-tert-butyl-silyl, diphenyl-tert-butyl silyl; or also groups such as tert-butoxycarbonyl, p-nitro-benzyloxycarbonyl, 2,2,2 trichloroethoxycarbonyl, benzyl and pyranyl.

When, in particular, the $R_6$ group is an alkyl or methylphenyl group substituted by hydroxy, preferred protecting group of the hydroxy function are p-nitrobenzyloxycarbonyl; dimethyl-tert-butyl silyl; diphenyl-tert-butyl silyl; trimethyl silyl; 2,2,2-trichloroethoxycarbonyl; benzyl; p-bromo-phenacyl; triphenylmethyl and pyranyl.

The radical $R_6'$ is an organic radical different from $R_6$ and can be a $C_1-C_4$ alkyl group such as the tertiary butyl group, or a $C_1-C_4$ alkoxy group, such as methoxy, ethoxy or isopropoxy. It may also be an arylalkoxy group such as benzyloxy or p-nitrobenzyloxy.

In a preferred embodiment Y is chlorine and $R_6$ is methyl or tert-butylidiphenylsilyloxymethyl.

$R_6$ is an organic radical and $R_6'$ is an organic radical different from $R_6$. Preferably Y is a chlorine atom, and $R_6$ is a methyl or tert-butyl-diphenylsilyloxymethyl group.

The product thereby obtained is an azetidinyl thioester of formula (V)

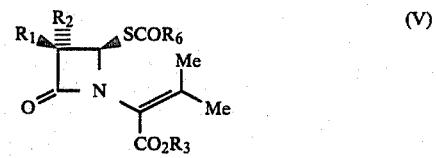

wherein $R_1$, $R_2$, $R_3$ and $R_6$ are defined as above.

The importance of azetidinyl thioesters in the synthesis of penems is well known (see, for example, I. Ernest in "Chemistry and Biology of β-Lactam Antibiotics", Morin and Gorman ed., Academic Press, NY, 1982, vol. 2, pp. 315–359); several routes from penams to these intermediates have been devised but they all suffer from major drawbacks (see M. Alpegiani et al., Tetrahedron Lett., 1983, 1638, 1627, and references therein). On the contrary, preparation of azetidinyl thioesters of formula (V) from penams according to the present invention is a single, high-yield, stereoselective one-pot process, exploiting as reagents the acyl chlorides of formula $R_6COCl$, handy and often commercially available compounds.

A particularly convenient procedure whcih for the first time elecits the synthesis of penem compounds of formula (VII) from penam compounds of formula (II) in a mere three-step process is herebelow described as illustrative of the merits of the present invention:

penam compound

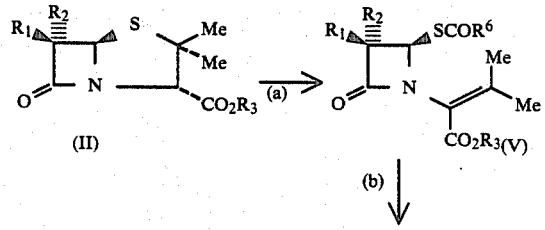

-continued
penem compound

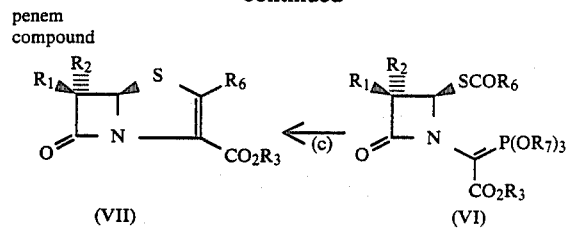

In step (a), the penam compound of formula (II) is converted into the azetidinyl thioester of formula (V) as above described. Conversion of the compound of formula (V) into a trialkoxyphosphorane of formula (IV), step (b), is simply accomplished by ozonolysis and quenching of the ozonide with excess trialkylphosphite $P(OR_7)_3$, wherein $R_7$ is a lower alkyl group, preferably ethyl or methyl, according to what is described by E. Perrone et al., Tetrahedron Lett., 1984, 2399. Just heating of the intermediates of formula (VI) then affords the desired penem of formula (VII).

EXAMPLE 1

Silver 3,3-dibromo-2-oxo-1-(trichloroethoxycarbonyl-2-methylprop-1-enyl)-(4R)-azetidinylthiolate A solution of trichloroethyl 6,6-dibromopenicillanate (1.01 g; 2.04 mmol) in acetonitrile (12 ml) was stirred at room temperature under argon in the presence of silver nitrate (0.41 mg, 2.4 mmol) and diazabicyclononene (0.29 ml, 2.4 mmol). After 3 hours all the starting material was converted into the title silver salt (TLC monitoring). Isolation of the latter was performed by partition between ethyl acetate and water. The organic layer was dried (MgSO$_4$), the solvent removed and the residue triturated in isopropyl ether to give a powder (700 mg); m.p. 160° (dec.).

IR=γmax (KBr) 1790, 1730 cm$^{-1}$.
NMR=δ(CDCl$_3$) 2.10 and 2.40 (each 3H, s, Me), 4.90 (2H, ABq, J=12 Hz, CH$_2$), 6.15 (1H, s, 4-H) ppm.
MS (FD)=593 m/z.

By following a similar procedure, but starting from p-nitrobenzyl 6,6-dibromopenicillanate, there was obtained silver 3,3-dibromo-1-(p-nitrobenzyloxycarbonyl-2-methylprop-1-enyl)-2-oxo-(4R)-azetidinylthiolate as a fine yellowish powder; m.p. 115°–120° C. (dec.).

IR=γmax (KBr) 1790, 1725 cm$^{-1}$.
NMR=δ(CDCl$_3$) 2.05 and 2.25 (each 3H, s, Me), 5.25 (2H, m, CH$_2$), 5.87 (1H, s, 4-H), 7.5 and 8.15 (each 2H, d, 8.5 Hz, Ar) ppm.

EXAMPLE 2

(4R)-acetylthio-3,3-dibromo-1-(trichloroethoxycarbonyl-2-methylprop-1-enyl)azetidin-2-one A solution of trichloroethyl 6,6-dibromopenicillanate (1 g) in acetonitrile (15 ml) was treated under argon with silver nitrate (416 ml) and diazabicyclononene (292 μl). After 3 hours at room temperature, acetyl chloride (174 μl) was added. A white precipitate of AgCl immediately appeared. After 10 minutes, the reaction mixture was filtered and poured into ethyl ether-aqueous 2% NaHCO$_3$ solution.

The organic layer was dried and evaporated to afford the crude title compound in quantitative yield. This material could be purified by silica gel chromatography; 0.89 g (82%); m.p. 87° C.

IR=γmax (KBr) 1795, 1745, 1720 cm$^{-1}$.

NMR=δ(CDCl$_3$) 2.05, 2.39, 2.45 (each 3H, s, Me), 4.88 (2H, s, CH$_2$CCl$_3$), 6.40 (1H, s, 4-H) ppm.

MS (FD)=529 m/z.

By following a similar procedure, but starting from p-nitrobenzyl 6,6-dibromopenicillanate, there was obtained (4R)-acetylthio-3,3-dibromo-1-(p-nitrobenzyloxycarbonyl-2-methylprop-2-enyl)azetidin-2-one, white powder; m.p. 110°-112° C.

IR=γmax (KBr) 1790, 1720, 1707 cm$^{-1}$.

NMR=δ(CDCl$_3$) 2.0, 2.31, 2.43 (each 3H, s, Me) 5.4 (2H, s, OCH$_2$Ar), 6.15 (1H, s, 4-H), 7.55 and 8.23 (each 2H, d, J=8.5 Hz, Ar) ppm; and starting from methyl 6,6-dibromopenicillanate, there was obtained (4R)-acetylthio-3,3-dibromo-1-(methoxycarbonyl-2-methylprop-1-enyl)azetidin-2-one; syrup.

IR=γmax (CHCl$_3$) 1790, 1725, 1710 sh. cm$^{-1}$.

NMR=δ(CDCl$_3$) 1.98, 2.30, 2.43 (each 3H, s, Me), 3.83 (3H, s, OMe), 6.22 (1H, s, 4-H) ppm; and starting from tert-butyl 6,6-dibromopenicillanate, there was obtained (4R)-acetylthio-3,3-dibromo-1-(tert-butoxycarbonyl-2-methylprop-1-enyl)azetidin-2-one; white powder; m.p. 180° C. (dec.).

IR=γmax (KBr) 1785, 1710 br cm$^{-1}$.

NMR=δ(CDCl$_3$) 1.55 (9H, s, C$_4$H$_9$), 1.95, 2.27, 2.43 (each 3H, s, Me), 6.30 (1H, s, 4-H) ppm; and starting from trichloroethyl 6α-bromo-6β-[(1R)-tert-butyldimethylsilyloxyethyl]penicillanate, there was obtained (4R)-acetylthio-(3S)-bromo-(3S)-[(1R)-tert-butyldimethylsilyloxyethyl]-1-(trichloroethoxycarbonyl-2-methylprop-1-enyl)azetidin-2-one.

IR=γmax (CHCl$_3$) 1780, 1730, 1700 cm$^{-1}$.

NMR=δ(CDCl$_3$) 0.13, 0.16 (each 3H, s, SiMe$_2$), 0.91 (9H, s, C$_4$H$_9$), 1.51 (3H, d, J=6 Hz, CH$_3$.CH), 2.02, 2.30, 2.36 (each 3H, s, Me), 4.83 (2H, s, CH$_2$CCl$_3$), 6.10 (1H, s, 4-H) ppm.

EXAMPLE 3

(4R)-tert-butyldiphenylsilyloxyacetylthio-3,3-dibromo-1-(trichloroethoxycarbonyl-2-methylprop-1-enyl)azetidin-2-one A solution of tert-butyldiphenylsilyloxyacetic acid (1.57 g) and thionyl chloride (0.72 ml) in dry benzene (25 ml) was kept at 25° C. for 24 hours. The reaction mixture was thoroughly evaporated and freed from the excess reagent and volatile by-products. In a separate vessel, trichloroethyl 6,6-dibromopenicillanate (2 g) in acetonitrile (12 ml) was sequentially treated in a nitrogen atmosphere with silver nitrate (0.83 g) and diazabicyclononene (0.584 ml). After 3 hour stirring at room temperature, a solution of the above-described acyl chloride in dry acetonitrile (10 ml) was dropped in under stirring; a white precipitate of silver chloride soon appeared. After a further 15 min., the reaction mixture was filtered and partitioned between water and ethyl acetate. The organic layer was washed with water, dried and evaporated to a syrup which was purified by flash-chromatography; 2.5 g (78%).

IR=γmax 1795, 1740, 1710 cm$^{-1}$.

NMR=δ(CDCl$_3$) 1.06 (9H, s, C$_4$C$_9$), 2.00 and 2.32 (each 3H, s, Me), 4.25 (2H, s, OCH$_2$CO), 4.80 (2H, s, OCH$_2$CCl$_3$), 6.30 (1H, s, H-4), 7.2–7.8 (10H, m, Ar) ppm.

EXAMPLE 4

(3S)-[(1R)-tert-Butyldimethylsilyloxyethyl](4R)-tert-butyldiphenylsilyloxyacetylthio-1-(trichloroethoxycarbonyl-2-methylprop-1-enyl)azetidin-2-one By following the experimental procedure described in Example 3, a solution of trichloroethyl 6α[(1R)-tert-butyldimethylsilyloxyethyl] penicillinate in MeCN was reacted with silver nitrate and diazabicyclononene (1 mol equiv. of each, 48 h, 0° C. in the dark, N$_2$), and the reaction mixture then treated with tert-butyldiphenylsilyloxyacetyl chloride (1.1 mol equiv., 1H, 20° C.) to afford to the title product (55% after silica gel chromatography).

IR=γmax (CHCl$_3$) 1760, 1725, 1695 cm$^{-1}$.

NMR=(200 MHz, CDCl$_3$)δ0.07, 0.10 (each 3H, s), 0.87, 1.06 (each 9H, s), 1.32 (3H, d, J=6.3 Hz) 2.03, 2.26 (each 3H, s) 3.35 (1H, dd, J=2.6 and 6.7 Hz), 4.19 (2H, s), 4.33 (1H, dq, J=6.7 and 6.3 Hz), 4.47, 4.85 (2H, each d, J=12.0 Hz), 5.76 (1H, d, J=2.6 Hz), 7.3–7.8 (10H, m).

EXAMPLE 5

(4R)-Acetylthio-(3S)-[(1R)-tert-butyldimethylsilyloxyethyl]-1-(1-trichloroethoxycarbonyl-2-methylprop-1-enyl)azetidin-2-one A solution of trichloroethyl 6α-](1R)-tert-butyldimethylsilyloxyethyl] penicillinate (450 mg; 0.92 mmol) in acetonitrile (15 ml) was added to a mixture of phenylmercuric chloride (313 mg; 1 mmol) and diazabicyclononene (0.118 ml; 0.95 mmol) in the same solvent (20 ml). After stirring for 2 h at room temperature, acetyl chloride (0.2 ml) was added, and the mixture was stirred for an additional hour, then partitioned between ethyl acetate and water. The organic layer was sequentially washed with 4% HCl, sat. NaHCO$_3$, H$_2$O, dried (Na$_2$SO$_4$) and evaporated. The residue was extracted with CCl$_4$ (15 ml); the insoluble salts were filtered off, and the solution was evaporated to give the title product in almost quantitative yield.

IR=γmax (CHCl$_3$) 1760, 1725, 1695 cm$^{-1}$.

NMR=(60 MHz, CDCl$_3$)δ0.10 (6H, s), 0.90 (9H, s), 1.30 (3H, d J=6.2 Hz), 2.03, 2.27, 2.32 (each 3H, s) 3.23 (1H, dd, J=2.5 and 6.5 Hz), 4.30 (1H, m), 4.80 (2H, s) 5.72 (1H, d, J=2.5 Hz).

Mass spectrum=531 (M+), 475 (M+-56, base peak).

EXAMPLE 6

(4R)-Acetylthio-(3R)-[(1R)-tert-butyldimethylsilyloxyethyl]-1-(1-trichloroethoxycarbonyl-2-methylprop-1-enyl)azetidin-2-one By following the experimental procedure described in Example 5, but starting from trichloroethyl 6β-[(1R)-tert-butyldimethylsilyloxyethyl] penicillinate, the title product was obtained in quantitative yield.

IR=γmax (CHCl$_3$) 1760, 1730, 1690 cm$^{-1}$.

NMR=(200 MHz, CDCl$_3$)δ0.09, 0.13 (each 3H, s,), 0.87 (9H, s) 1.39 (3H, d, J=6.4 Hz), 1.98, 2.21, 2.28 (each 3H, s), 3.58 (1H, dd, J=2.9 and 5.7 Hz), 4.10 (1H, qd, J=2.9 and 6.4 Hz), 4.76, 4.84 (2H, each d, J=12.0 Hz), 5.93 (1H, d, J=5.7 Hz).

I claim:

1. A process for preparing a compound of the formula I:

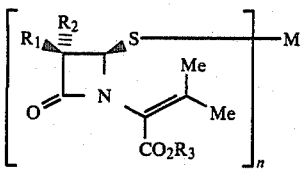

(I)

wherein
R$_1$ and R$_2$ are each independently hydrogen or halogen or substituted or unsubstituted C$_1$-C$_4$ alkyl groups, the optional substituents may be selected from hydroxy, amino, cyano, mercapto and trifluoromethyl groups, wherein the hydroxy, amino and mercapto group may be free or protected;

R$_3$ is hydrogen or a C$_{1-4}$ alkyl group, halo substituted C$_{1-4}$ alkyl group, C$_{2-4}$ alkenyl group, aryl group, aryl-C$_{1-6}$ alkyl group, aryloxy C$_{1-4}$ alkyl group, benzhydryl, o-nitrobenzhydryl, acetonyl, trimethylsilyl, diphenyl tertiary butylsilyl, dimethyltertiary butylsilyl, alkanoylmethyl, or arylcarboxy;

n is 1 or 2;

M represents Ag$^I$ or a heavy metal M$_1$ in the +2 oxidation state selected from the group consisting of Cu$^{II}$, Hg$^{II}$ or Pb$^{II}$, or a group M$_2$A wherein M$_2$ is a heavy metal in the +2 oxidation state selected from the group consisting of Cu$^{II}$, Hg$^{II}$ or Pb$^{II}$ and A is lower alkanoyloxy, aryl or an ion of an inorganic acid which comprises treating a compound of formula II

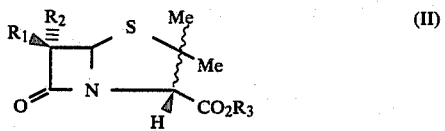

(II)

wherein R$_1$, R$_2$ and R$_3$ are defined as above, with a strong, poorly nucleophilic base and an organic or inorganic salt of the heavy metal M$_1$ or of the M$_2$A aggregate, wherein M$_1$, M$_2$ and A are as defined above, in a aprotic organic solvent at a temperature of from −70° to 100° C.

2. A process according to claim 1, wherein said strong, poorly nucleophilic base is selected from diazabicyclononene, 1,4-diazabicyclo octane and diazabicycloundecene.

3. A process according to claim 1, wherein said organic or inorganic salt of the heavy metal M$_1$ is silver nitrate, silver perchlorate, silver acetate or mercury acetate.

4. A process according to claim 1 wherein said organic salt of the M$_2$A aggregate is methoxycarbonylmercury (II) acetate, or phenyl mercury (II) chloride.

5. A process according to claim 1 wherein said aprotic organic solvent is acetonitrile, dimethylformamide, benzene or dichloromethane.

6. A process according to claim 1 wherein the reaction is carried out at 15°-25° C.

7. A process according to claim 1, in which R$_1$, R$_2$ are each independently a bromo or hydrogen atom or protected 1-hydroxy ethyl group and R$_3$ is methyl, t-butyl, trichloroethyl or p-nitrobenzyl group.

8. A process according to claim 1, in which the compound of formula (I) is acylated with a compound of formula R$_6$COY, wherein Y represents a chlorine atom, OCOR$_6$, OCOR$_6'$ or imidazolyl group, R$_6$ represents a substituted or unsubstituted C$_{1-4}$ alkyl, methyl-phenyl or methyl C$_{5-7}$ cycloalkyl group, wherein the substituents are selected from the group comprising protected or unprotected hydroxy, amino or carbamoyloxy groups, halogen atoms, or heterocyclylthio, wherein the heterocyclylthio is unsubstituted or substituted by amino, hydroxy, oxo or a C$_{1-4}$ alkyl group, and R$_6'$ is a C$_1$-C$_4$ alkyl, C$_1$-C$_4$ alkoxy or arylalkoxy group, to give an azetidinyl thioester of the formula:

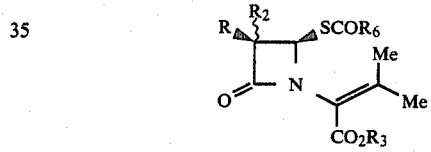

where R$_1$, R$_2$ and R$_3$ are as defined in claim 1 and R$_6$ is as defined above.

9. A process according to claim 8, in which Y represents a chlorine atom and R$_6$ is methyl or tert-butyldiphenylsilyloxymethyl group.

* * * * *